United States Patent
Omura et al.

(10) Patent No.: US 8,269,051 B2
(45) Date of Patent: Sep. 18, 2012

(54) WICKEROL AND METHOD FOR PRODUCING THE SAME

(75) Inventors: Satoshi Omura, Tokyo (JP); Kazuro Shiomi, Tokyo (JP); Rokuro Masuma, Tokyo (JP); Hideaki Ui, Kanagawa (JP); Takayuki Nagai, Tokyo (JP); Haruki Yamada, Tokyo (JP)

(73) Assignee: The Kitasato Institute, Tokyo (JP)

( * ) Notice: Subject to any disclaimer, the term of this patent is extended or adjusted under 35 U.S.C. 154(b) by 215 days.

(21) Appl. No.: 12/933,162

(22) PCT Filed: Mar. 12, 2009

(86) PCT No.: PCT/JP2009/055367
§ 371 (c)(1),
(2), (4) Date: Sep. 17, 2010

(87) PCT Pub. No.: WO2009/116604
PCT Pub. Date: Sep. 24, 2009

(65) Prior Publication Data
US 2011/0021848 A1    Jan. 27, 2011

(30) Foreign Application Priority Data
Mar. 17, 2008    (JP) .................................. 2008-067498

(51) Int. Cl.
*C07C 35/08*    (2006.01)
*C07C 35/06*    (2006.01)
*A01N 31/00*    (2006.01)
*C12P 7/00*    (2006.01)

(52) U.S. Cl. ......... 568/832; 568/838; 514/729; 435/132

(58) Field of Classification Search .................. None
See application file for complete search history.

(56) References Cited

U.S. PATENT DOCUMENTS
5,202,244 A    4/1993    Hiramitsu et al.

FOREIGN PATENT DOCUMENTS
JP    49-020389    2/1974
JP    4-094693    3/1992

OTHER PUBLICATIONS

Sun et al., Journal of Natural Medicines (2011), 65(2), 381-384.*
International Search Report, PCT/JP2009/055367,May 26, 2009.
Hideaki Ui et al., "Shijokin no Seisan suru Shinki Ko-Influenza Virus Busshitsu no Tanri, Kozo Oyobi Kassei", Abstracts of 128th Annual Meeting of Pharmaceutical Society of Japan 2, Mar. 5, 2008, p. 126.
Fukami A. et al., A new anti-influenza virus antiboitic, 10-norparvulenone from *Microspaeropsis* sp. FO-5050, J. Antibiot., Oct. 2000, vol. 53, No. 10, pp. 1215-1218.

* cited by examiner

*Primary Examiner* — Karl J Puttlitz
(74) *Attorney, Agent, or Firm* — Young & Thompson

(57) ABSTRACT

The present invention includes wickerol and a method for producing the wickerol. In the method for producing the wickerol, *Trichoderma atroviride* strain FKI-3737 (FERM ABP-11099 corresponding to FERM BP-11099) belonging to filamentous fungi is cultured in a medium, and the wickerol is accumulated in a culture, and then the produced wickerol is isolated and purified from the culture. A substance having inhibitory activity against influenza virus replication and containing the wickerol as an active ingredient, and an anti-influenza drug containing the wickerol as an active ingredient are obtained.

5 Claims, No Drawings

WICKEROL AND METHOD FOR PRODUCING THE SAME

TECHNICAL FIELD

The present invention relates to a novel substance, wickerol, effective to be used in pharmaceutical products and veterinary drugs due to its inhibitory activity against influenza virus replication, and a method for producing the wickerol.

BACKGROUND ART

Human influenza epidemics occur almost every year around the world while influenza viruses mutate. In addition, human influenza pandemics occur roughly every several tens of years, causing several millions to several tens of millions of deaths. It is well known that highly pathogenic avian H5N1 influenza virus, now causing outbreaks among poultry mainly in Asian countries, is feared as a cause of the next pandemic. At present, to prevent damages to humans caused by influenza viruses, vaccination or drugs are used. However, during an epidemic caused by a novel influenza virus, it is extremely difficult to prevent infections with vaccines, which require epidemic assessment, and the vaccines cannot be used for treatment after the onset of the influenza.

Therapeutic drugs for influenza are indispensable. Four anti-influenza drugs acting at either of two sites of action, namely, neuraminidase and M2 ion channel, are currently available, specifically, Oseltamivir (F. Hoffmann-La Roche Ltd., Switzerland), Zanamivir (GlaxoSmithKline, United Kingdom), Amantadine (Novartis International AG, Switzerland), and Rimantadine (Forest Laboratories, Inc., U.S.A.).

Only three of the above anti-influenza drugs are approved in Japan. However, the above-described drugs are not sufficient for a potential pandemic because of drug resistant strains and issues such as administration routes, a spectrum of influenza virus subtypes, and side effects.

Social concerns in development of a novel anti-influenza drug are extremely high. To take countermeasures against new strains and drug resistant strains, it is important to have multiple drugs which differ in structure and site of action. However, a novel drug which differs from existing drugs in structure and site of action has not been suggested, and is highly desired.

The onset of the influenza is caused by explosive replication of the influenza virus with symptoms such as inflammation and fever. Because the influenza virus infects the cells to replicate inside the cells, the explosive replication of the influenza virus is inhibited by blocking a life cycle of the influenza virus in any phase from binding of the influenza virus to the cell to budding and maturation of the influenza virus. A substance having the ability to block the life cycle of the influenza virus is highly promising as a substance having inhibitory activity against influenza virus replication and as an anti-influenza drug, capable of preventing the onset of the influenza or alleviating the symptoms of the influenza.

The present invention is researched and developed in view of the foregoing, and the present invention satisfies the expectations for the substance having inhibitory activity against influenza virus replication and the anti-influenza drug. An object of the present invention is to obtain wickerol that is a substance cultured using *Trichoderma atroviride* strain FKI-3737 (FERMABP-11099 corresponding to FERM BP-11099) and then isolated and purified from the culture, and also to provide a substance having inhibitory activity against influenza virus replication and containing the wickerol as an active ingredient, and an anti-influenza drug containing the wickerol as an active ingredient.

DISCLOSURE OF INVENTION

As a result of the search in a culture of a microorganism for a substance which inhibits replication process of influenza virus through infection of cells, the inventors of the present invention found that the novel substance wickerol produced by filamentous fungal strain FKI-3737, isolated from soil by the inventors, has the inhibitory activity against the replication process of the influenza virus through the infection of cells. The present invention has been completed based on these findings.

The present invention has been completed based on these findings, and provides the wickerol represented by the following formula of claim 1.

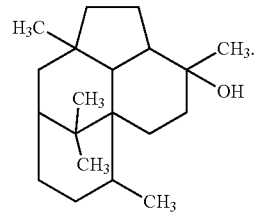

The present invention provides a method for producing the wickerol comprising the steps of culturing in a medium a microorganism belonging to filamentous fungi of claim 2 and having the ability to produce the wickerol of claim 1, and accumulating the wickerol in a culture, and obtaining the wickerol from the culture.

The present invention provides the method for producing the wickerol in which the microorganism having the ability to produce the wickerol of claim 2 is *Trichoderma atroviride* FKI-3737 (FERM ABP-11099 corresponding to FERN BP-11099).

The present invention provides *Trichoderma atroviride* strain FKI-3737 (FERM ABP-11099 corresponding to FERN BP-11099) of claim 4.

The present invention provides a substance having inhibitory activity against replication of influenza virus, and the substance contains the wickerol represented by the following formula of claim 5 as an active ingredient.

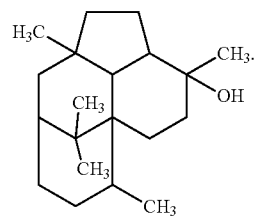

The present invention provides an anti-influenza drug having the wickerol represented by the following formula of claim 6 as an active ingredient.

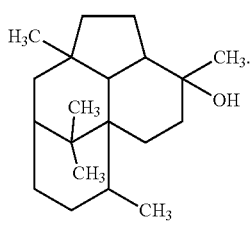

A microorganism having the ability to produce the wickerol of the present invention (hereinafter may referred to as FKI-3737 substance producing microorganism) belongs to *Trichoderma atroviride*. For example, *Trichoderma atroviride* strain FKI-3737, newly isolated from soil by the inventors of the present invention, is one of the most effective strains used in the present invention. Mycological properties of *Trichoderma atroviride* strain FKI-3737 of the present invention are as follows.

1. Morphological Properties

The strain showed good growth on potato dextrose agar, cornmeal dextrose agar, wort agar, and the like. Good adhesion of conidia was observed on each of the above media. Microscopic observation of colonies grown on the potato dextrose agar shows that hyphae are transparent and septa are formed. Conidiophores arise from basal hyphae, and bear phialides at their tips. Each phialide is 7.5-12.5×2.0-2.8 µm in size, verticillate in whorls of 3 to 5, and short and thick. Conidia are borne at the tips of the phialides and form viscous globules. Each conidium is globose or aglobose in shape, with smooth surface, 2.3-2.8×2.3-3.0 µm in size.

2. Properties on Various Agar Media

The strain is cultured in various agar media for 3 days at 25° C. Results of macroscopic observation are shown in Table 1 below.

TABLE 1

| medium | growth on medium (radius of colony) | color of surface of colony | color of reverse of colony | soluble pigment |
|---|---|---|---|---|
| potato dextrose agar | good (65 to 69 mm), floccose, filamentous at the periphery | white | white | none |
| cornmeal dextrose agar | good (34 to 37 mm), floccose, filamentous at the periphery | colorless to white | colorless to white | none |
| wort agar | good (65 to 67 mm), floccose, filamentous at the periphery | white | white | none |
| synthetic nutrient agar | good (53 to 55 mm), floccose, filamentous at the periphery | colorless | colorless | none |

3. Physiological Properties (1) Optimum Growth Condition

The optimum growth condition of the strain is pH 3-6 at 16.0-30.0° C.

(2) Growth Range

The growth range of the strain is pH 2-8 at 10.0-32.0° C.

(3) Aerobic or Anaerobic: Aerobic

As a result of comparison of the morphological properties, the culture properties, and the physiological properties between the above described strain FKI-3737 and known strains, the strain FKI-3737 was identified as a strain belonging to *Trichoderma atroviride*, and was named *Trichoderma atroviride* FKI-3737. Microbial Resource Center of Kitasato Institute for Life Sciences at Kitasato University deposited the strain as *Trichoderma atroviride* FKI-3737 in International Patent Organism Depositary, National Institute of Advanced Industrial Science and Technology, of AIST Tsukuba Central 6, 1-1, Higashi 1-chome Tsukuba-shi, Ibaraki-ken 305-8566 Japan, on Mar. 6, 2008. The accession number was FERM P-21520. Thereafter, according to the Budapest Treaty on the International Recognition of the Deposit of Microorganisms for the Purpose of Patent Procedure, a transfer to international deposition was requested to the above-mentioned International Patent Organism Depositary, National Institute of Advanced Industrial Science and Technology on Feb. 23, 2009 and accepted. The reception number was FERM ABP-11099 (the accession number was FERM BP-11099).

The above described *Trichoderma atroviride* strain FKI-3737 is the most preferable example of the FKI-3737 substance producing microorganism used in the present invention. Generally, however, mycological properties of the microorganism are extremely mutable and not stable. Any strain of filamentous fungi, including genetically engineered strains and spontaneous mutant strains, having the ability to produce the wickerol of the present invention under natural conditions or through common processes such as UV irradiation or X-ray irradiation can be used in the present invention.

To produce the wickerol of the present invention, first, a microorganism belonging to filamentous fungi having the ability to produce the wickerol is cultured. Then, the wickerol is isolated and purified from the culture. Any strain of FKI-3737 substance producing microorganism belonging to filamentous fungi, including the above described strains and their mutant strains, can be used in the present invention.

Any nutrient source usable for filamentous fungi is suitable as the nutrient source for the FKI-3737 substance producing microorganism. For example, nitrogen sources such as commercially available peptone, meat extract, corn steep liquor, cottonseed powder, peanut powder, soybean meal, yeast extract, NZ-amine, casein hydrates, sodium nitrate, ammonium nitrate and ammonium sulfate, carbohydrates such as glycerin, starch, glucose, galactose and mannose, carbon sources such as fat, and inorganic salts such as sodium chloride, phosphate, calcium carbonate and magnesium sulfate can be used alone or in combination.

If necessary, trace metal salts, and an antifoam agent such as animal oil, vegetable oil or mineral oil can be added. Any known culture material for the filamentous fungi can be used as long as the culture material can be used by the FKI-3737 substance producing microorganism and is useful for the production of the wickerol. The cultivating temperature of the wickerol is maintained in a range in which the FKI-3737 substance producing microorganism is able to grow and produce the wickerol. The cultivating conditions are selected among those described above depending on the properties of FKI-3737 substance producing microorganism.

With the use of a water immiscible organic solvent such as chloroform and ethyl acetate, the wickerol is extracted from a culture liquid. In addition to the above extracting method, known methods used for extracting fat-soluble substance, such as adsorption chromatography, gel filtration chromatography, scraping of the thin layer chromatography, centrifugal countercurrent chromatography and high performance liquid chromatography can be used in combination or in repetition as necessary to obtain the purified wickerol.

Physicochemical properties of the wickerol of the present invention are as follows.

(1) Nature: white powder (2) Molecular weight: 290.2605 (M+, measured by high resolution electron ionization mass spectrometry)

(3) Molecular formula: $C_{20}H_{34}O$ (4) Specific rotation: $[\alpha]^{31}=-2.8°$ (c=0.1, methanol)

(5) UV absorption spectrum in methanol: only end absorption was observed.

(6) Infrared absorption spectrum (Kbr tablet): maximum absorption at 3319, 2954, 2929, 2875, 2360, 1734 $cm^{-1}$.

(7) $^1H$ nuclear magnetic resonance spectrum: chemical shifts (ppm) in deuterated chloroform and spin coupling constants (Hz) are shown in Table 2.

(8) $^{13}C$ nuclear magnetic resonance spectrum: chemical shifts (ppm) in deuterated chloroform are shown in the Table 2.

(9) Solubility in solvent: easily soluble in n-hexane, chloroform, acetone, and ethanol. Soluble in methanol and 2-propanol. Insoluble in water.

(10) Color reaction: positive to phosphomolybdic acid-sulfuric acid reaction.

TABLE 2

| $^{13}$C-NMR | $^1$H-NMR |
|---|---|
| 73.9 s | |
| 52.0 d | 1.27 d (1H, J = 13.4) |
| 44.4 d | 1.87 ddd (1H, J = 6.1, 10.0, 13.4) |
| 43.9 t | 1.41 brd (1H, J = 11.2) |
| | 1.00 brd (1H, J = 11.2) |
| 43.0 t | 1.68 dd (1H, J = 4.2, 12.3) |
| | 1.49 m (1H) |
| 41.1 d | 1.48 m (1H) |
| 40.8 t | 1.58 ddd (1H, J = 3.5, 3.6, 12.8) |
| | 1.44 m (1H) |
| 39.2 s | |
| 38.8 s | |
| 38.7 s | |
| 28.8 t | 2.00 dddd (1H, J = 2.6, 11.2, 11.2, 15.5) |
| | 1.46 m (1H) |
| 26.6 d | 2.11 m (1H) |
| 26.4 t | 1.69 m (1H) |
| | 1.21 ddd (1H, J = 3.5, 14.2, 14.2) |
| 25.7 t | 2.09 m (1H) |
| | 1.62 m (1H) |
| 25.6 q | 0.94 s (3H) |
| 24.6 q | 1.05 s (3H) |
| 22.9 d | 1.02 d (3H, J = 7.0) |
| 21.6 t | 1.79 m (1H) |
| | 1.58 m (1H) |
| 20.5 d | 1.17 s (3H) |
| 19.9 d | 1.05 s (3H) |

[Notes]
s: singlet, d: doublet, dd: double doublet, ddd: double double doublet, dddd: double double double doublet, t: triplet, q: quartet, m: multiplet, brd: broad doublet, H: the number of protons, J: spin coupling constant (unit: Hz)

As a result of examination of various physicochemical properties and spectral data of the wickerol of the present invention, the structure of the wickerol is determined to be represented by the following formula.

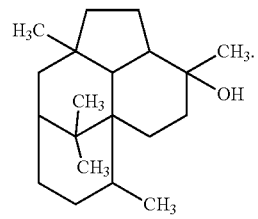

As described above, various physicochemical properties of the wickerol are detailed, and no compound having the same properties as the wickerol has been reported. Therefore, the wickerol is identified as a novel substance.

Next, inhibitory activity of the wickerol of the present invention against replication of influenza virus through infection of cells is described.

An assay for the influenza virus replication through the infection of cells was performed as follows. In each well of a 48-well microplate (Becton, Dickinson and Co., USA), 50,000 Madin-Darby canine kidney cells (MDCK cells) were plated as a suspension in 500 µl of cell culture medium [9.5 g/l MEM (Gibco 61100-053, U.S.A.) and 10% fetal bovine serum (Hyclone, USA)]. The MDCK cells were cultured for two days in 5% carbon dioxide at 37° C.

Next, the cell culture medium was removed, and each well was washed twice with 500 µl of phosphate buffer solution (PBS; containing 137 mM sodium chloride, 8.1 mM disodium hydrogenphosphate, 2.68 mM potassium chloride, and 1.47 mM potassium dihydrogen phosphate). Thereafter, influenza virus suspended in 500 µl of a medium (for infection) was added to each well. The medium for infection contains 9.4 g/l Eagle's MEM (Nissui 05901, Japan), 0.1% dextrose, 3 µg/ml acetylated trypsin, 0.3 mg/ml L-glutamine, 1 ml/l vitamin solution (Gibco 11120-052, U.S.A.), 1 µg/ml folic acid, 1 µg/ml biotin, 3 mg/ml HEPES, 2.5 µg/ml amphotericin B, 200 µg/ml gentamicin, 2.25 mg/ml sodium bicarbonate, and 2 mg/ml bovine serum albumin.

A paraffin paper (6 mm in diameter) was soaked with a sample dissolved in a solvent and then dried, and thereafter added to each well. The cells were further cultured for 3 days in 5% carbon dioxide at 37° C., while the microplate was gently shaken using a shaker (Wave-PR, Titec, Japan). After the cultivation, the medium was removed, and each well was washed twice with 500 µl of PBS. Then, 25% glutaraldehyde (72.5 µl) was added to fix the cells for 10 minutes at room temperature. After supernatants were removed, each well was washed twice with 500 µl of PBS. Then, 0.05% crystal violet solution (125 µl) was added, and color reaction was performed for 15 minutes at room temperature.

After the supernatants are removed, each well was washed for four times with 500 µl of PBS. Then, 0.5% SDS solution (500 µl) was added, and stirred and dissolved in each well. The dissolved solution (100 µl) was taken from each well and put into a 96-well plate. To each well, 100 µl of PBS was added. The cell viability was assayed by measuring UV absorption at 595 nm using a microplate reader (ELx 808, BioTek instruments Inc., U.S.A.). Inhibition activity of the wickerol against the replication of the influenza virus through the infection of cells was calculated in comparison to a control experiment in which a paraffin paper, soaked only with the solvent at the time of adding the sample and then dried, was added and processed in the same manner as the above.

As a result, the wickerol inhibited the replication of influenza virus A/PR/8/34 through the infection of the MDCK cells with $IC_{50}$=70 ng/ml. On the other hand, the wickerol inhibited the proliferation of the MDCK cells alone with $IC_{50}=7$ μg/ml. Thus, the wickerol exhibited inhibitory activity against the influenza virus replication approximately 100 times as high as cytotoxicity.

Antimicrobial activity of the wickerol of the present invention was as follows. Each circular filter paper (Advantec, diameter: 6 mm) was soaked with 10 μl of methanol solution of the wickerol (1 mg/ml), and then allowed to air-dry for a predetermined time to remove a solvent. After the solvent was removed, the circular filter paper was placed on each of the following test microorganism-containing agar plates, and cultured for 24 hours at 35° C. Thereafter, a diameter of a growth inhibitory circle formed around each of the circular filter papers was measured, and the results were shown in Table 3.

TABLE 3

| Test microorganism | inhibitory diameter (unit: mm) |
| --- | --- |
| Staphylococcus aureus ATCC6538p | − |
| Bacillus subtilis ATCC6633 | − |
| Micrococcus luteus ATCC9341 | ± |
| Mycobacterium smegmatis ATCC607 | − |
| Escherichia coli NIHJ | − |
| Escherichia coli NIHJ JC-2 (IF012734) | − |
| Pseudomonas aeruginosa IF03080 | − |
| Xanthomonas campestris pv. oryzae KB88 | − |
| Bacteroides fragilis ATCC23745 | − |
| Acholeplasma laidrawii KB174 | − |
| Candida albicans KF1 | − |
| Saccharomyces cerevisiae KF26 | − |
| Pyricularia oryzae KF 180 | ± |
| Aspergillus niger ATCC6275 | − |
| Mucor racemosus IF04581 | − |

The wickerol of the present invention exhibited almost no antimicrobial activity against the microorganisms shown in the Table 3. Therefore, the wickerol of the present invention can be used as a substance inhibiting influenza virus replication through infection of cells or as a pharmaceutical drug such as an anti-influenza drug.

EFFECT OF THE INVENTION

As described above, a novel substance wickerol, a substance derived from a filamentous fungal strain FKI-3737 and a method for producing the substance according to the present invention are obtained by a microbiological method. The obtained substance can be effectively used as a substance having the inhibitory activity against influenza virus replication and as a pharmaceutical drug such as an anti-influenza drug.

BEST MODE FOR CARRYING OUT THE INVENTION

Hereinafter, the present invention is described specifically with referring to examples. However, the present invention is not limited to them.

One loopful of Trichoderma atroviride FKI-3737 (FERM ABP-11099 corresponding to FERM BP-11099) cultured on an agar slant medium was inoculated into a 500 ml Erlenmeyer flask containing 100 ml of a liquid medium (pH 6.0) consisting of 2.0% glucose, 0.5% polypeptone (Nihon Pharmaceutical Company, Ltd., Japan), 0.2% yeast extract (Oriental Yeast Co., Ltd., Japan), 0.1% agar, 0.1% potassium dihydrogen phosphate, and 0.05% magnesium sulfate heptahydrate, and then shake-cultured for 2 days at 27° C.

The obtained seed culture liquid was inoculated 1 ml each into 90 flasks of 500 ml Erlenmeyer flasks each containing 100 ml of a liquid medium (pH 6.5) consisting of 3.0% soluble starch, 1.0% glycerol, 2.0% soybean meal, 0.3% dried yeast (Fermipan, GB Ingredients, Netherlands), 0.2% calcium carbonate, 0.05% potassium dihydrogen phosphate, 0.05% magnesium sulfate heptahydrate, and then shake-cultured for 4 days at 27° C.

After the cultivation, 100 ml of ethanol was added to each of the 90 flasks of 500 ml Erlenmeyer flasks, and the liquid in each flask was stirred vigorously for one hour. Next, ethanol in the extraction liquid was evaporated at reduced pressure, and the pH of the obtained aqueous solution was adjusted to 9 using sodium hydroxide. Then, from the obtained aqueous solution, a crude material was extracted with an equal amount of n-hexane, and concentrated and dried. Thus, 1.38 g of the crude material was obtained. Of the obtained crude material, 0.70 g was placed on a silica gel column (φ2.2×15.0 cm) packed with n-hexane, and eluted with n-hexane-acetone (100:5). Fractions exhibiting the intended activity were recovered and subjected to vacuum concentration, and thus 25.3 mg of wickerol was obtained as white powder.

INDUSTRIAL APPLICABILITY

The present invention relates to wickerol and a method for producing the wickerol comprising the steps of culturing in a medium a microorganism belonging to filamentous fungi and having the ability to produce the wickerol, and accumulating the wickerol in a culture, and obtaining the wickerol from the culture. The obtained wickerol is effectively used as a substance having inhibitory activity against the replication of influenza virus, and as a pharmaceutical drug such as an anti-influenza drug.

The invention claimed is:

1. Wickerol represented by the formula:

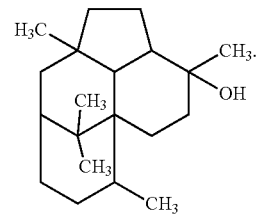

2. A method for producing wickerol comprising the steps of culturing in a medium a microorganism belonging to filamentous fungi and having ability to produce the wickerol of claim 1, and accumulating the wickerol in a culture, and obtaining the wickerol from the culture.

3. The method of claim 2, wherein the microorganism having the ability to produce the wickerol is Trichoderma atroviride FKI-3737 (FERN ABP-11099 corresponding to FERN BP-11099).

4. A combination having inhibitory activity against influenza virus replication, the combination containing wickerol as an active ingredient, the wickerol being represented by the formula:

9
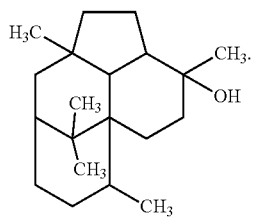
10
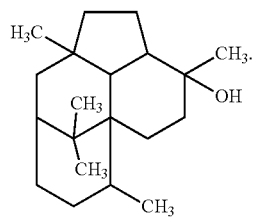
5. An anti-influenza drug having wickerol as an active ingredient, the wickerol represented by the formula:
* * * * *